(12) United States Patent
Ohno et al.

(10) Patent No.: US 8,426,427 B2
(45) Date of Patent: Apr. 23, 2013

(54) FUSED HETEROCYCLIC DERIVATIVE, PHARMACEUTICAL COMPOSITION COMPRISING THE DERIVATIVE, AND USE OF THE COMPOSITION FOR MEDICAL PURPOSES

(75) Inventors: Kohsuke Ohno, Azumino (JP); Noboru Kamada, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 638 days.

(21) Appl. No.: 12/595,931

(22) PCT Filed: Apr. 16, 2008

(86) PCT No.: PCT/JP2008/057391
§ 371 (c)(1),
(2), (4) Date: Oct. 14, 2009

(87) PCT Pub. No.: WO2008/133127
PCT Pub. Date: Nov. 6, 2008

(65) Prior Publication Data
US 2010/0081674 A1 Apr. 1, 2010

(30) Foreign Application Priority Data
Apr. 18, 2007 (JP) ................................. 2007-108935

(51) Int. Cl.
*C07D 495/04* (2006.01)
*A61K 31/519* (2006.01)
*A61P 25/28* (2006.01)
*A61P 35/00* (2006.01)

(52) U.S. Cl.
USPC ........................................ 514/260.1; 544/278

(58) Field of Classification Search .................. 544/278; 514/260.1
See application file for complete search history.

(56) References Cited

U.S. PATENT DOCUMENTS

| 5,817,819 A | 10/1998 | Furuya et al. |
| 2001/0031865 A1 | 10/2001 | Klintz et al. |
| 2002/0132820 A1 | 9/2002 | Zhu et al. |
| 2007/0010537 A1 | 1/2007 | Hamamura et al. |
| 2009/0062258 A1 | 3/2009 | Hamamura et al. |

FOREIGN PATENT DOCUMENTS

| EP | 1939204 A1 | 7/2008 |
| JP | 6-510992 T | 12/1994 |
| WO | 95/28405 A1 | 10/1995 |
| WO | 96/24594 A1 | 8/1996 |
| WO | 00/39131 A1 | 7/2000 |
| WO | 01/55119 A2 | 8/2001 |
| WO | 2005/019188 A1 | 3/2005 |
| WO | 2006/083005 A1 | 8/2006 |
| WO | 2007/046392 A1 | 4/2007 |

OTHER PUBLICATIONS

Banker, G.S. et al, "Modern Pharmaceutics, 3 ed." Marcel Dekker, New York, 1996, p. 596.*
Wolff, Manfred E. "Burger's Medicinal Chemistry, 5ed, Part I", John Wiley & Sons, 1995, pp. 975-977.*
Dorwald, F. A. Side Reactions in Organic Synthesis, 2005, Wiley: VCH, Weinheim p. IX of Preface.*

* cited by examiner

*Primary Examiner* — Susanna Moore
(74) *Attorney, Agent, or Firm* — Sughrue Mion, PLLC

(57) ABSTRACT

The present invention provides compounds useful as agents for the prevention or treatment of a sex hormone-dependent disease or the like. That is, the present invention provides fused heterocyclic derivatives represented by the following general formula (I) which has a GnRH antagonistic activity, pharmaceutical compositions containing the same, medicinal uses thereof and the like. In the formula (I), rings A is 5-membered cyclic unsaturated hydrocarbon or 5-membered heteroaryl; $R^A$ is halogen, alkyl, alkenyl, alkynyl, carboxy, alkoxy, carbamoyl, alkylcarbamoyl, etc.; ring B is aryl or heteroaryl; $R^B$ is halogen, alkyl, carboxy, alkoxy, carbamoyl, alkylcarbamoyl, etc.; $E^1$ and $E^2$ are oxygen atom, etc.; Q is hydrogen atom, alkyl, alkylsulfonyl, acyl, etc.; X is -(alkylene)-Z, —CO—Y, —$SO_2$—Y, etc. (in which Y is Z or amino, etc.; Z is cycloalkyl, heterocycloalkyl, aryl, heteroaryl, etc.

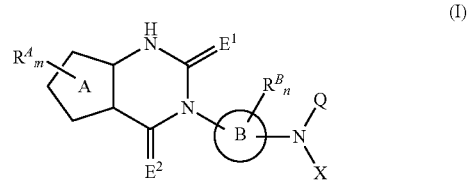

(I)

10 Claims, No Drawings

FUSED HETEROCYCLIC DERIVATIVE, PHARMACEUTICAL COMPOSITION COMPRISING THE DERIVATIVE, AND USE OF THE COMPOSITION FOR MEDICAL PURPOSES

CROSS REFERENCE TO RELATED PATENT APPLICATIONS

This application is a National Stage of International Application No. PCT/JP2008/057391 filed Apr. 16, 2008, claiming priority based on Japanese Patent Application No. 2007-108935, filed Apr. 18, 2007, the contents of all of which are incorporated herein by reference in their entirety.

TECHNICAL FIELD

The present invention relates to fused heterocyclic derivatives.

More particularly, the present invention relates to fused heterocyclic derivatives which have an antagonistic activity against gonadotropin releasing hormone and can be used for the prevention or treatment of a sex hormone-dependent disease such as benign prostatic hypertrophy, hysteromyoma, endometriosis, metrofibroma, precocious puberty, amenorrhea, premenstrual syndrome, dysmenorrhea or the like, or prodrugs thereof, or pharmaceutically acceptable salts thereof, and pharmaceutical compositions containing the same and the like.

BACKGROUND ART

Gonadotropin Releasing Hormone (GnRH, or it is also called Luteinizing Hormone Releasing Hormone: LHRH, hereinafter referred to as "GnRH") is a peptide consisting of 10 amino acids: pGlu-His-Trp-Ser-Tyr-Gly-Leu-Arg-Pro-Gly-NH$_2$), which is secreted from the hypothalamus. GnRH secreted into hypophyseal portal vein promotes the production and secretion of gonadotropin of anterior pituitary hormones, Luteinizing Hormone: LH and Follicle Stimulating Hormone: FSH, via the receptors which are considered to exist in the anterior lobe of the pituitary, GnRH receptor. These gonadotropins affect gonad, ovary and testis, to promote the follicular growth, ovulation and luteinization and spermatogenesis and also promote the production and secretion of sex hormones such as estrogen, progesterone and androgen (see Non-patent reference 1). Accordingly, antagonists specifically and selectively acting on the GnRH receptors should control the activities of GnRH and control the production and secretion of gonadotropin and sex hormones, and therefore, are expected to be useful as an agent for the prevention or treatment of sex hormone-dependent diseases.

As an agent inhibiting the function of GnRH receptor, GnRH receptor superagonists (hereinafter referred to as "GnRH superagonist") have been used as agents for the treatment of sex hormone-dependent diseases such as pro static cancer, breast cancer, endometriosis and the like. The GnRH superagonists bind GnRH receptors and exert an initial temporary gonadotropin secretion-stimulating effect so-called "flare-up phenomenon", and then suppress the function by causing gonadotropin depletion and GnRH receptor down-regulation to suppress. Therefore, the GnRH receptor superagonists have a problem that the disease becomes exacerbated transiently by the initially promoted secretion of gonadotropin. On the other hand, the suppression mechanism of GnRH receptor antagonists (hereinafter referred to as "GnRH antagonist") is an inhibition of the binding to GnRH receptors, and therefore, are expected to exert promptly suppressive effects without secretion of gonadotropin. In these years, as GnRH antagonists, peptidic GnRH antagonists such as abarelix and cetrorelix have been developed and used for the treatment of prostatic cancer, infertility and the like. However, since these peptidic GnRH antagonists have bad oral absorbability, they have to be subcutaneously or intramuscularly administered. Thus, development of a non-peptidic GnRH antagonist which can be orally administered wherein local reactivity at injected sites can be reduced and the dosages can be flexibly adjusted is desired (see Non-patent reference 2).

As fused pyrimidine derivatives having a non-peptidic GnRH antagonistic activity, compounds described in Patent references 1 and 2 and the like are known. However, all compounds described in Patent reference 1 have an aryl substituent on the 5-membered hetero ring fused with a pyrimidine ring. In addition, compounds described in Patent reference 2 are pyrimidine derivatives fused with a 6-membered aromatic ring and their oral absorbability is necessarily high. In Patent reference 3 recently published, pyrimidine derivatives fused with a 5-membered hetero ring having a non-peptidic GnRH antagonistic activity are described. However, there are no specific description about compounds other than that having a sulfonamide or amide group, and there are no specific description about pharmacokinetics in blood by oral administration.

As compounds having a pyrimidine ring fused with a 5-membered hetero ring, in addition to the above, various compounds are illustrated as serine protease inhibitors in Patent reference 4, blood coagulation factor Xa inhibitors in Patent reference 5 and herbicides in Patent reference 6, respectively. However, in any of these references, there are no descriptions or suggestion about that that a compound having a pyrimidine ring fused with a 5-membered hetero ring of the present invention has a GnRH antagonistic activity.

Non-patent reference 1: Hyojun Seirigaku (Standard Physiology), Edition 5, Igakusyoin, pp. 882-891.

Non-patent reference 2: Sanka to Fujinka (Obstetrics and Gynecology), 2004, Vol. 71, No. 3, pp. 280-285 and 301-307.

Patent reference 1: International publication No. WO1996/24597 pamphlet.

Patent reference 2: International publication No. WO2005/019188 pamphlet.

Patent reference 3: International publication No. WO2006/083005 pamphlet.

Patent reference 4: U.S. patent application publication No. 2003/0004167 description.

Patent reference 5: International publication No. WO00/39131 pamphlet.

Patent reference 6: Japanese patent publication No. Tokuhyo-Hei6-510992 (JP H06-510992 T) pamphlet.

DISCLOSURE OF THE INVENTION

Objects to be Solved by the Invention

The present invention aims to provide a compound which has a GnRH antagonistic activity.

Means for Solving the Problems

The present inventors have studied earnestly to solve the above problems. As a result, it was found that a pyrimidine derivative fused with a 5-membered hetero ring represented by the following general formula (I) has an excellent GnRH antagonistic activity and exerts an excellent pharmacokinetics in blood by oral administration in comparison with a pyrimidine derivative fused with a 6-membered aromatic ring, thereby forming the basis of the present invention.

That is, the present invention relates to:

[1] a fused heterocyclic derivative represented by the general formula (I):

[Chem.1]

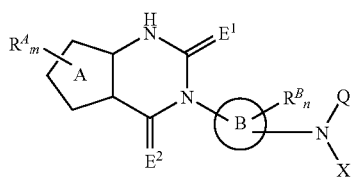

(I)

wherein ring A represents 5-membered cyclic unsaturated hydrocarbon or 5-membered heteroaryl;

$R^A$ represents a halogen atom, a cyano group, a nitro group, an optionally substituted lower alkyl group, an optionally substituted lower alkenyl, group, an optionally substituted lower alkynyl group, a hydroxyiminomethyl group, an optionally substituted (lower alkyl)sulfonyl group, an optionally substituted (lower alkyl)sulfinyl group, a tetrazolyl group, —$OW^1$, —$SW^1$, —$COW^1$, —$COOW^1$, —$NHCOW^1$, —$NHCONW^2W^3$, —$NW^2W^3$, —$CONW^2W^3$ or —$SO_2NW^2W^3$, in which $W^1$ to $W^3$ independently represent a hydrogen atom or an optionally substituted lower alkyl group, or $W^2$ and $W^3$ optionally bind together to form an optionally substituted cyclic amino group with the neighboring nitrogen atom;

m represents an integer number 0 to 3;

ring B represents aryl or heteroaryl;

$R^B$ represents a halogen atom, a cyano group, an optionally substituted lower alkyl group, —$OW^4$, —$COW^4$, —$COOW^4$ or —$CONW^5W^6$, in which $W^4$ to $W^6$ independently represent a hydrogen atom or an optionally substituted lower alkyl group, or $W^5$ and $W^6$ optionally bind together to form an optionally substituted cyclic amino group with the neighboring nitrogen atom;

n represents an integer number 0 to 2;

$E^1$ represents an oxygen atom, a sulfur atom or N—CN;

$E^2$ represents an oxygen atom or NH;

Q represents a hydrogen atom, an optionally substituted lower alkyl group, —$COW^7$, —$SO_2W^8$, an optionally substituted aryl group, an optionally substituted heteroaryl group, an optionally substituted cycloalkyl group or an optionally substituted heterocycloalkyl group with the proviso that Q and $R^B$ optionally bind together to form an optionally substituted heterocycloalkyl group;

X represents a group represented by -L-Z, —CO—Y, —$SO_2$—Y, -L-CO—Z, —CO-L-Y or —$SO_2$-L-Y, in which $W^7$ represents a hydrogen atom, an optionally substituted lower alkyl group, an optionally substituted lower alkoxy group, —$NW^9W^{10}$, an optionally substituted aryl, group, an optionally substituted heteroaryl group, an optionally substituted cycloalkyl group or an optionally substituted heterocycloalkyl group, wherein $W^9$ and $W^{10}$ independently represent a hydrogen atom or an optionally substituted lower alkyl group, or $W^9$ and $W^{10}$ optionally bind together to form an optionally substituted cyclic amino group with the neighboring nitrogen atom;

$W^8$ represents an optionally substituted lower alkyl group, an optionally substituted aryl group, an optionally substituted heteroaryl group, an optionally substituted cycloalkyl group or an optionally substituted heterocycloalkyl group;

L represents an optionally substituted lower alkylene group;

Y represents a group represented by Z or —$NW^{11}W^{12}$, wherein $W^{11}$ and $W^{12}$ independently represent a hydrogen atom, an optionally substituted lower alkyl group or Z with the proviso that $W^{11}$ and $W^{12}$ are not hydrogen atoms at the same time, or $W^{11}$ and $W^{12}$ optionally bind together to form an optionally substituted cyclic amino group with the neighboring nitrogen atom;

Z represents an optionally fused and optionally substituted cycloalkyl group, an optionally fused and optionally substituted heterocycloalkyl group, an optionally fused and optionally substituted aryl group or an optionally fused and optionally substituted heteroaryl group; and with the proviso that when X is -L-Z, and Z is optionally substituted aryl or optionally substituted heteroaryl, the aryl or heteroaryl has at least one substituent; or a prodrug thereof, or a pharmaceutically acceptable salt thereof;

[2] a fused heterocyclic derivative as described in the above [1], wherein ring A is a 5-membered heteroaryl ring, or a prodrug thereof, or a pharmaceutically acceptable salt thereof;

[3] a fused heterocyclic derivative as described in the above [2], wherein the 5-membered heteroaryl ring of ring A is any one of thiophene rings represented by the formula:

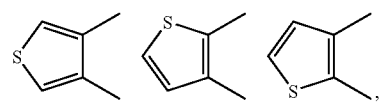

[Chem.2]

or a prodrug thereof, or a pharmaceutically acceptable salt thereof;

[4] a fused heterocyclic derivative as described in the above [3], wherein the 5-membered heteroaryl ring of ring A is any one of thiophene rings represented by the formula:

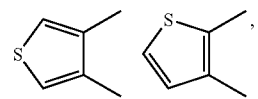

[Chem.3]

or a prodrug thereof, or a pharmaceutically acceptable salt thereof;

[5] a fused heterocyclic derivative as described in any of the above [1] to [4], wherein $R^A$ is a halogen atom, an optionally substituted lower alkyl group, —$COOW^1$ or —$CONW^2W^3$ in which $W^1$ to $W^3$ independently represent a hydrogen atom or an optionally substituted lower alkyl group, or $W^2$ and $W^3$ optionally bind together to form an optionally substituted cyclic amino group with the neighboring nitrogen atom, or a prodrug thereof, or a pharmaceutically acceptable salt thereof;

[6] a fused heterocyclic derivative as described in the above [5], wherein $R^A$ is a lower alkyl group substituted by a group selected from the group consisting of a hydroxy group, a carboxy group and a carbamoyl group; a carboxy group; or a carbamoyl group, or a prodrug thereof, or a pharmaceutically acceptable salt thereof;

[7] a fused heterocyclic derivative as described in any of the above [1] to [6], wherein m is 0 or 1, or a prodrug thereof or a pharmaceutically acceptable salt thereof;

[8] a fused heterocyclic derivative as described in the above [7], wherein m is 1 and ring A having $R^A$ on the ring is any of thiophene rings represented by the following formula:

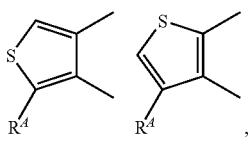
[Chem.4]

or a prodrug thereof, or a pharmaceutically acceptable salt thereof;

[9] a fused heterocyclic derivative as described in any of the above [1] to [8], wherein $E^1$ is an oxygen atom, or a prodrug thereof, or a pharmaceutically acceptable salt thereof;

[10] a fused heterocyclic derivative as described in any of the above [1] to [9], wherein $E^2$ is an oxygen atom, or a prodrug thereof, or a pharmaceutically acceptable salt thereof;

[11] a fused heterocyclic derivative as described in any of the above [1] to [10], wherein ring B is a benzene ring, a thiophene ring or a pyridine ring, or a prodrug thereof, or a pharmaceutically acceptable salt thereof;

[12] a fused heterocyclic derivative as described in the above [11], wherein ring B is any of rings represented by the formula:

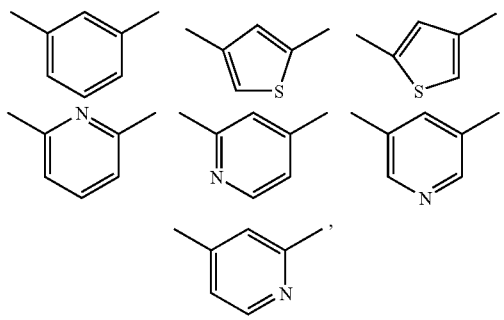
[Chem. 5]

or a prodrug thereof, or a pharmaceutically acceptable salt thereof;

[13] a fused heterocyclic derivative as described in the above [12], wherein n is 1 or 2 and ring B having $R^B$ on the ring is any of benzene rings, pyridine rings and thiophene rings represented by the following formula:

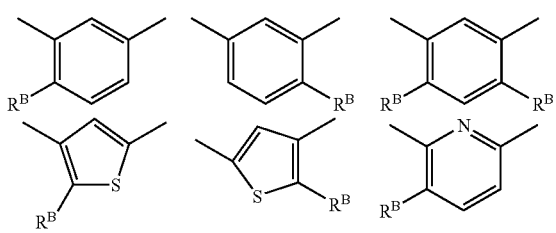
[Chem. 6]

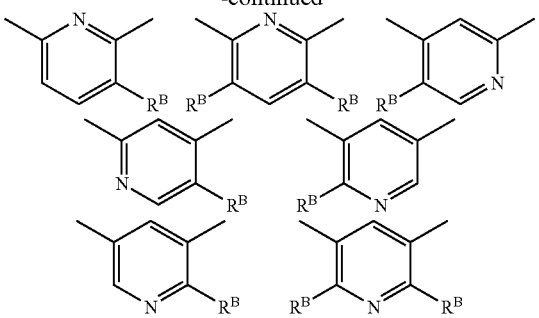
-continued in the formula, $R^B$ has the same meaning as defined above, and when two $R^B$ exist, these two $R^B$ may be the same or different from each other, or a prodrug thereof, or a pharmaceutically acceptable salt thereof;

[14] a fused heterocyclic derivative as described in the above [12] or [13], wherein ring B is any of rings represented by the formula:

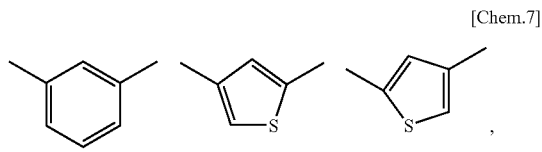
[Chem.7]

or a prodrug thereof, or a pharmaceutically acceptable salt thereof;

[15] a fused heterocyclic derivative as described in any of the above [1] to [14], wherein $R^B$ is a halogen atom, an optionally substituted lower alkyl group, —$OW^4$ in which $W^4$ is a hydrogen atom or an optionally substituted lower alkyl group, or a cyano group, or a prodrug thereof, or a pharmaceutically acceptable salt thereof;

[16] a fused heterocyclic derivative as described in the above [15], wherein $R^B$ is a halogen atom, a lower alkyl group optionally substituted by a halogen atom, or —$OW^4$ in which $W^4$ is a hydrogen atom or an optionally substituted lower alkyl group, or a prodrug thereof, or a pharmaceutically acceptable salt thereof;

[17] a fused heterocyclic derivative as described in the above [16], wherein $R^B$ is a fluorine atom, a chlorine atom or —$OW^4$ in which $W^4$ is a lower alkyl group, or a prodrug thereof, or a pharmaceutically acceptable salt thereof;

[18] a fused heterocyclic derivative as described in any of the above [1] to [17], wherein X is a group represented by -L-Z in which L and Z have the same meanings as defined above, or a prodrug thereof, or a pharmaceutically acceptable salt thereof;

[19] a fused heterocyclic derivative as described in any of the above [1] to [18], wherein Q is a hydrogen atom, an optionally substituted lower alkyl group, —$COW^7$ or —$SO_2W^8$ in which $W^7$ is an optionally substituted lower alkyl group or an optionally substituted lower alkoxy group, and $W^8$ is an optionally substituted lower alkyl group, or a prodrug thereof, or a pharmaceutically acceptable salt thereof;

[20] a fused heterocyclic derivative as described in the above [19], wherein Q is an optionally substituted lower alkyl group, or a prodrug thereof, or a pharmaceutically acceptable salt thereof;

[21] a fused heterocyclic derivative as described in any of the above [1] to [20], wherein L is a $C_{1-3}$ alkylene group, or a prodrug thereof, or a pharmaceutically acceptable salt thereof;

[22] a fused heterocyclic derivative as described in any of the above [1] to [21], wherein Z is an optionally fused and optionally substituted aryl group, or a prodrug thereof, or a pharmaceutically acceptable salt thereof;

[23] a pharmaceutical composition comprising as an active ingredient a fused heterocyclic derivative as described in any of the above [1] to [22], or a prodrug thereof, or a pharmaceutically acceptable salt thereof;

[24] a pharmaceutical composition as described in the above [23], which is a gonadotropin releasing hormone antagonist;

[25] a pharmaceutical composition as described in the above [23], which is an agent for the prevention or treatment of a sex hormone-dependent disease, a reproduction regulator, a contraceptive, an ovulation inducing agent or an agent for the prevention of post-operative recurrence of sex hormone-dependent cancers;

[26] a pharmaceutical composition as described in the above [25], wherein the sex hormone-dependent disease is selected from the group consisting of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor;

[27] a pharmaceutical composition as described in any of the above [23] to [26], wherein the composition is an oral formulation;

[28] a pharmaceutical composition as described in any of the above [23] to [27], which comprises a combination with at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent;

[29] a pharmaceutical composition as described in the above [28], wherein the GnRH superagonist is selected from the group consisting of leuprorelin acetate, gonadorelin, buserelin, triptorelin, goserelin, nafarelin, histrelin, deslorelin, meterelin and lecirelin;

[30] a pharmaceutical composition as described in the above [28], wherein the chemotherapeutic agent is selected from the group consisting of ifosfamide, adriamycin, peplomycin, cisplatin, cyclophosphamide, 5-FU, UFT, methotrexate, mitomycin C, mitoxantrone, paclitaxel and dotaxel;

[31] a pharmaceutical composition as described in the above [28], wherein the peptidic GnRH antagonist is selected from the group consisting of cetrorelix, ganirelix, abarelix, ozarelix, iturelix, degarelix and teverelix;

[32] a pharmaceutical composition as described in the above [28], wherein the 5α-reductase inhibitor is selected from the group consisting of finasteride and dutasteride;

[33] a pharmaceutical composition as described in the above [28], wherein the α-adrenoceptor inhibitor is selected from the group consisting of tamsulosin, silodosin and urapidil;

[34] a pharmaceutical composition as described in the above [28], wherein the aromatase inhibitor is selected from the group consisting of fadrozole, letrozole, anastrozole and formestane;

[35] a pharmaceutical composition as described in the above [28], wherein the adrenal androgen production inhibitor is liarozole;

[36] a pharmaceutical composition as described in the above [28], wherein the hormonotherapeutic agent is selected from the group consisting of an antiestrogenic agent, a progestational agent, an androgenic agent, an estrogenic agent and an antiandrogenic agent; and the like.

Effects of the Invention

Since a fused heterocyclic derivative (I) of the present invention or a prodrug thereof, or a pharmaceutically acceptable salt thereof, has an excellent GnRH antagonistic activity, it can control the effect of gonadotropin releasing hormone and control the production and secretion of gonadotropin and sex hormones, and as a result, it can be used as an agent for the prevention or treatment of sex hormone-dependent diseases.

BEST MODE TO PUT THE INVENTION TO PRACTICE

Meanings of terms used in this description are as follows.

The term "5-membered cyclic unsaturated hydrocarbon" means a 5-membered hydrocarbon ring having 1 or 2 double bonds.

The term "heteroaryl" means monocyclic heteroaryl having 1 or more hetero atoms selected from the group consisting of a nitrogen atom, an oxygen atom and a sulfur atom such as thiazole, oxazole, isothiazole, isoxazole, pyridine, pyrimidine, pyrazine, pyridazine, pyrrole, furan, thiophene, imidazole, pyrazole, oxadiazole, thiadiazole, triazole, tetrazole, furazan or the like.

The term "optionally substituted" means which may have a substituent.

The term "5-membered heteroaryl" means the above heteroaryl, which is 5-membered monocyclic, for examples, thiazole, oxazole, isothiazole, isoxazole, pyrrole, furan, thiophene, imidazole, pyrazole, oxadiazole, thiadiazole, triazole, tetrazole, furazan and the like can be illustrated.

The term "aryl" means phenyl.

The term "halogen atom" means a fluorine atom, a chlorine atom, a bromine atom or a iodine atom.

The term "lower alkyl" means optionally branched alkyl having 1 to 6 carbon atoms such as methyl, ethyl, propyl, isopropyl, butyl, isobutyl, sec-butyl, tert-butyl, pentyl, isopentyl, neopentyl, tert-pentyl, hexyl or the like.

The term "lower alkenyl" means optionally branched alkenyl having 2 to 6 carbon atoms such as vinyl, allyl, 1-propenyl, isopropenyl, 1-butenyl, 2-butenyl, 2-methylallyl or the like.

The term "lower alkynyl" means optionally branched alkynyl having 2 to 6 carbon atoms such as ethynyl, 2-propynyl or the like.

The term "(lower alkyl)sulfonyl" means sulfonyl substituted by the above lower alkyl.

The term "(lower alkyl)sulfinyl" means sulfinyl substituted by the above lower alkyl.

The term "lower alkylene" means optionally branched alkylene having 1 to 6 carbon atoms such as methylene, ethylene, methylmethylene, trimethylene, dimethylmethylene, ethylmethylene, methylethylene, propylmethylene, isopropylmethylene, dimethylethylene, butylmethylene, ethylmethylmethylene, pentamethylene, diethylmethylene, dimethyltrimethylene, hexamethylene, diethylethylene or the like.

The term "$C_{1-3}$ alkylene" means the above lower alkylene having 1 to 3 carbon atoms.

The term "lower alkoxy" means optionally branched alkoxy having 1 to 6 carbon atoms such as methoxy, ethoxy, propoxy, isopropoxy, butoxy, isobutoxy, sec-butoxy, tent-butoxy, pentyloxy, isopentyloxy, neopentyloxy, tert-pentyloxy, hexyloxy or the like.

The term "(lower alkoxy)carbonyl" means an optionally branched alkoxycarbonyl group having 2 to 7 carbon atoms.

The term "(lower alkyl)thio" means optionally branched alkylthio having 1 to 6 carbon atoms.

The term "cycloalkyl" means monocyclic cycloalkyl having 3 to 8 carbon atoms, for example, monocyclic cycloalkyl such as cyclopropyl, cyclobutyl, cyclopentyl, cyclohexyl, cycloheptyl, cyclooctyl and the like can be illustrated.

The term "heterocycloalkyl" means 3 to 8-membered heterocycloalkyl having 1 or more hetero atoms selected from the group consisting of a nitrogen atom, an oxygen atom and a sulfur atom and optionally having 1 or 2 oxo groups such as pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl, oxazolidinyl or the like. In case of having a sulfur atom in the ring, the sulfur atom may be oxidized.

The term "optionally fused" means which may be fused with a ring selected from the group consisting of the above cycloalkyl, the above heterocycloalkyl, the above aryl and the above heteroaryl. As "fused cycloalkyl", "fused heterocycloalkyl", "fused aryl" and "fused heteroaryl", for example, indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, naphthyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl and the like can be illustrated, and the free valency may be on either ring.

The term "cyclic amino" means a group having at least a nitrogen atom which is a binding site in the ring among the above optionally fused heterocycloalkyl. For example, 1-pyrrolidinyl, 1-piperidinyl, 1-piperazinyl, 4-morpholinyl, 4-thiomorpholinyl, 2,3,4,5,6,7-hexahydro-1H-azepin-1-yl, 1-indolinyl, 2-isoindolinyl, 3,4-dihydro-1,5-naphthyridin-1(2H)-yl, 1,2,3,4-tetrahydroquinolin-1-yl, 3,4-dihydroquinolin-1(2H)-yl, 3,4-dihydroisoquinolin-2(1H)-yl, octahydroquinolin-1(2H)-yl, octahydroisoquinolin-2(1H)-yl, perhydroquinolin-1-yl, 2,3-dihydro-4H-1,4-benzoxazin-4-yl, 2,3-dihydro-4H-1,4-benzothiazin-4-yl, 3,4-dihydroquinoxalin-1(2H)-yl, 2,3-dihydro-4H-pyrid[3,2-b][1,4]oxazin-4-yl, 2,3,4,5-tetrahydro-1H-1-benzoazepin-1-yl, 1,3,4,5-tetrahydro-2H-2-benzoazepin-2-yl, 3,4-dihydro-1,5-benzoxazepin-5(2H)-yl, 2,3-dihydro-4,1-benzothiazepin-1(5H)-yl, 3,4-dihydro-1,5-benzothiazepin-5(2H)-yl, 2,3-dihydro-4,1-benzoxazepin-1(5H)-yl, 2,3,4,5-tetrahydro-1H-1,5-benzodiazepin-1-yl, 2,3,4,5-tetrahydro-1H-1,4-benzodiazepin-1-yl, 5,6,7,8-tetrahydro-4H-thieno[3,2-b]-azepin-4-yl, 3,4,5,6-tetrahydro-1-benzazocin-1(2H)-yl and the like can be illustrated.

The term "(di)(lower alkyl)amino" means amino mono- or di-substituted by the above lower alkyl. Two lower alkyl groups in di-substituted amino may be different and the two lower alkyl groups may bind together to form a cyclic amino group with the neighboring nitrogen atom.

The term "(di)(lower alkyl)carbamoyl" means carbamoyl mono- or di-substituted by the above lower alkyl. Two lower alkyl groups in di-substituted carbamoyl may be different and the two lower alkyl groups may bind together to form a cyclic amino group with the neighboring nitrogen atom.

The term "acyl" means optionally branched aliphatic carboxylic acyl having 2 to 7 carbon atoms, cycloalkylcarboxylic acyl, heterocycloalkylcarboxylic acyl, arylcarboxylic acyl, or heteroarylcarboxylic acyl.

The term "acylamino" means amino substituted by the above acyl.

In the general formula (I), as ring A, 5-membered heteroaryl is preferable, a thiophene ring is more preferable, and thiophene rings represented by the following formula:

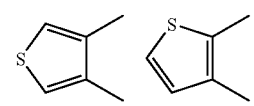

[Chem.8]

are particularly preferable. As $R^4$, a halogen atom, an optionally substituted lower alkyl group, —$COOW^1$, —$CONW^2W^3$ in which $W^1$ to $W^3$ independently represent a hydrogen atom or an optionally substituted lower alkyl group, or $W^2$ and $W^3$ optionally bind together to form an optionally substituted cyclic amino group with the neighboring nitrogen atom, or the like is preferable, a lower alkyl group substituted by a group selected from the group consisting of a hydroxy group, a carboxy group and a carbamoyl group; a carboxy group; or a carbamoyl group is more preferable, and a carboxy group is even more preferable. In case that m is 2 or more, these $R^4$ may be the same or different. m is preferably 0 or 1, and in case that m is 1, as ring A having $R^4$ on the ring, thiophene rings represented by the following formula:

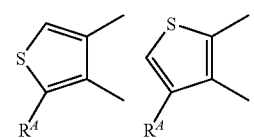

[Chem.9]

are particularly preferable. In this case, as $R^4$, an optionally substituted lower alkyl group, —$COOW^1$ or —$CONW^2W^3$ in which $W^1$ to $W^3$ independently represent a hydrogen atom or an optionally substituted lower alkyl group, or $W^2$ and $W^3$ optionally bind together to form an optionally substituted cyclic amino group with the neighboring nitrogen atom, is more preferable.

In the general formula (I), as $E^1$, an oxygen atom is preferable, and, as $E^2$, an oxygen atom is preferable.

In the general formula (I), as ring B, a benzene ring, a thiophene ring or a pyridine ring is preferable, and a benzene ring or a thiophene ring is more preferable. In this case, the binding position of ring B is preferably as represented by the following formula:

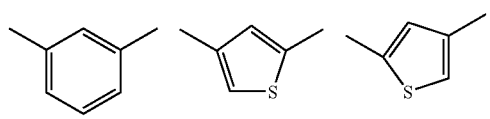

[Chem.10]

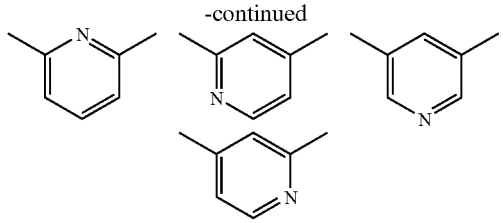

and in particular, is preferably as represented by the following formula:

[Chem. 11]

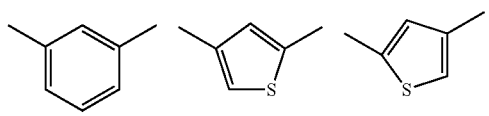

wherein the left bond represents a bond with the nitrogen atom of the fused pyrimidine ring and the right bond represents a bond with the nitrogen atom of —N(Q)(X).

In case that n is 1 or 2, as ring B having $R^B$ on the ring, a benzene ring, a thiophene ring or a pyridine ring represented by the following formula:

[Chem. 12]

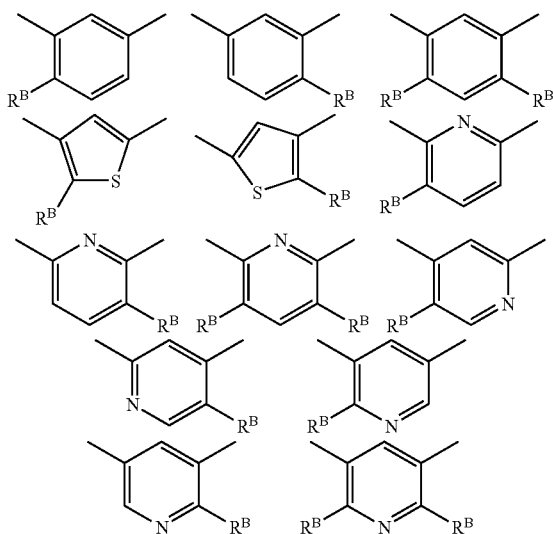

wherein the left bond of the bonds not bound to any of $R^B$ represents a bond with the nitrogen atom of the fused pyrimidine ring and the right bond represents a bond with the nitrogen atom of —N(Q)(X) is preferable. As $R^B$, a halogen atom, an optionally substituted lower alkyl group, —$OW^4$ in which $W^4$ represents a hydrogen atom or an optionally substituted lower alkyl group, a cyano group or the like is preferable, a halogen atom, a lower alkyl group which may be substituted by a halogen atom or —$OW^4$ is more preferable, and a fluorine atom, a chlorine atom or —$OW^4$ in which $W^4$ is a lower alkyl group is particularly preferable. In case that n is 2, two $R^B$ may be the same or different. In addition, in case that ring B having $R^B$ on the ring is a benzene ring, a thiophene ring or a pyridine ring represented by the following formula:

[Chem. 13]

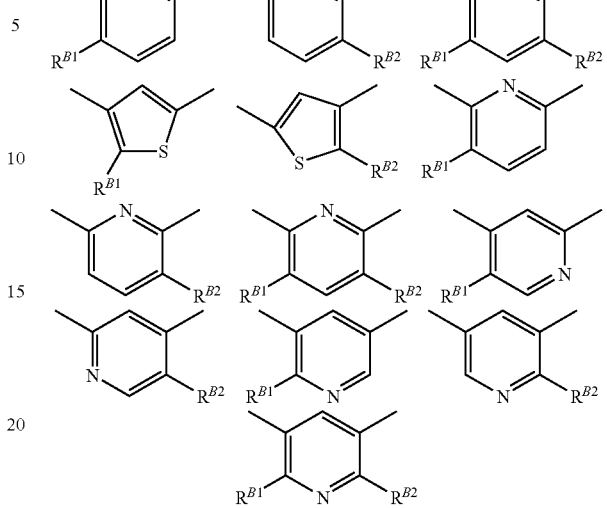

wherein the left bond of the bonds not bound to any of $R^{B1}$ and $R^{B2}$ represents a bond with the nitrogen atom of the fused pyrimidine ring and the right bond represents a bond with the nitrogen atom of —N(Q)(X), as $R^{B1}$, a fluorine atom or a chlorine atom is preferable, and as $R^{B2}$, a fluorine atom, a methoxy group or an ethoxy group is preferable, and a methoxy group is more preferable.

In the general formula (I), as X, a group represented by -L-Z wherein L represents an optionally substituted lower alkylene group; Z represents an optionally fused, and optionally substituted cycloalkyl group, an optionally fused and optionally substituted heterocycloalkyl group, an optionally fused and optionally substituted aryl group or an optionally fused and optionally substituted heteroaryl group with the proviso that when Z is an optionally substituted aryl group or an optionally substituted heteroaryl group, the aryl group or heteroaryl group has at least a substituent, is preferable.

As Q, a hydrogen atom, an optionally substituted lower alkyl group, —$COW^7$ or —$SO_2W^8$ wherein $W^7$ represents an optionally substituted lower alkyl group or an optionally substituted lower alkoxy group, $W^8$ represents an optionally substituted lower alkyl group, is preferable, and an optionally substituted lower alkyl group is more preferable.

As L, a $C_{1-3}$ lower alkylene group is more preferable.

As Z, an optionally fused and optionally substituted heteroaryl group or an optionally fused and optionally substituted aryl group is more preferable, and an optionally fused and optionally substituted aryl group is more preferable. In Z, as a substituent which an optionally substituted heteroaryl group or an optionally substituted aryl group may have, a halogen atom, an optionally substituted lower alkyl group or an optionally substituted lower alkoxy group is preferable, and a halogen atom; a lower alkyl group optionally substituted by a halogen atom, a lower alkoxy group or a hydroxy group; or a lower alkoxy group optionally substituted by a halogen atom, a lower alkoxy group or a hydroxy group, is more preferable.

As a substituent which an optionally substituted cyclic amino group, an optionally substituted cycloalkyl group or an optionally substituted heterocycloalkyl group may have, for example, an oxo group, a halogen atom, a cyano group, a hydroxy group, an optionally substituted lower alkyl group, a cycloalkyl group, an optionally substituted lower alkoxy group, an optionally substituted (lower alkyl)thio group, a carboxy group, an optionally substituted (lower alkoxy)carbonyl group, a carbamoyl group, a (di)(lower alkyl)carbamoyl group, an optionally, substituted aryl group, an aryloxy group, a heteroaryl group, a heteroaryloxy group, an acylamino group and the like can be illustrated, and the same or different two or more groups selected from these groups may exist with the proviso that as a substituent which an optionally substituted cyclic amino group —NW²W³ forms in R^A may have, any groups having an aryl group are excluded.

As a substituent which an optionally substituted aryl or an optionally substituted heteroaryl group may have, for example, a halogen atom, a nitro group, a cyano group, a hydroxy group, an optionally substituted lower alkyl group, a cycloalkyl group, an optionally substituted lower alkoxy group, an optionally substituted (lower alkyl)thio group, a carboxy group, an optionally substituted (lower alkoxy)carbonyl group, a carbamoyl group, a (di)(lower alkyl)carbamoyl group, an aryl group, an aryloxy group, a heteroaryl group, a heteroaryloxy group, an acylamino group and the like can be illustrated, and the same or different two or more groups selected from these groups may exist.

In an optionally fused and optionally substituted cycloalkyl group, an optionally fused and optionally substituted heterocycloalkyl group, an optionally fused and optionally substituted aryl group and an optionally fused and optionally substituted heteroaryl group, the above substituents optionally exist on the same or different rings in the fused ring.

As a substituent which an optionally substituted lower alkyl, an optionally substituted lower alkylene, an optionally substituted lower alkenyl, an optionally substituted lower alkynyl, an optionally substituted (lower alkyl)sulfonyl, an optionally substituted (lower alkyl)sulfinyl, an optionally substituted lower alkoxy, an optionally substituted (lower alkyl)thio or an optionally substituted (lower alkoxy)carbonyl group may have, a halogen atom, a cyano group, a hydroxy group, a lower alkoxy group, a (lower alkyl)thio group, an amino group, a (di)(lower alkyl)amino group, a carboxy group, a (lower alkoxy)carbonyl group, a carbamoyl group, a (di)(lower alkyl)carbamoyl group, an aryl group, a heteroaryl group and the like can be illustrated, and the same or different two or more groups selected from these groups may exist with the proviso that in R^A, any groups having an aryl group or groups having a heteroaryl group are excluded.

An example of the methods for preparing a fused heterocyclic derivative represented by the general formula (I) of the present invention is shown below.

[Method 1]

Among the fused heterocyclic derivatives represented by the general formula (I) of the present invention, a compound wherein E¹ is an oxygen atom can be prepared, for example, by Method 1.

[Chem. 14]

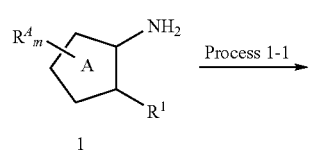

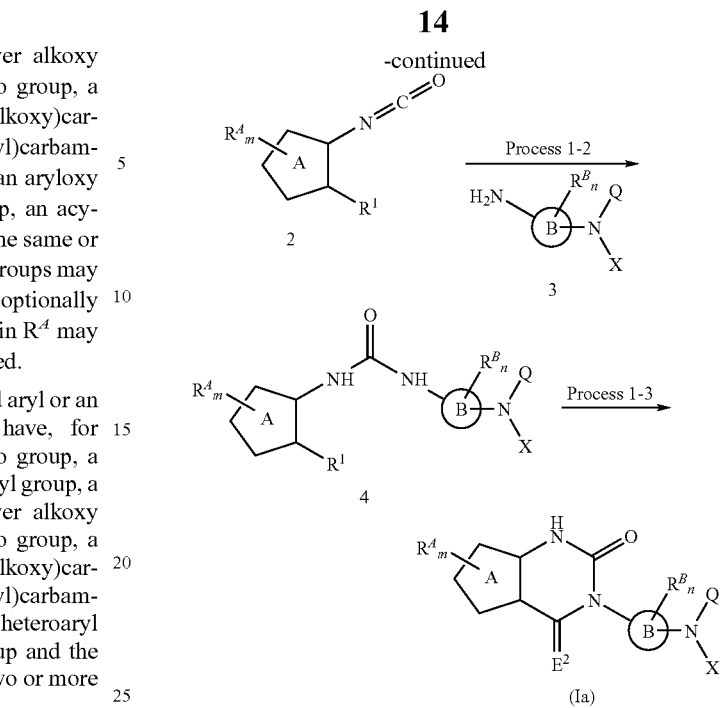

In the formula, R¹ represents a nitrile group or a (lower alkoxy)carbonyl group; ring A, ring B, R^A, R^B, m, n, E², Q and X have the same meanings as defined above.

Process 1-1

Amine compound (1) can be converted by allowing to react in, an inert solvent such as tetrahydrofuran, methylene chloride, a mixed solvent thereof or the like using a reagent such as phosgene, diphosgene, triphosgene or the like in the presence of a base such as triethylamine, N,N-diisopropylethylamine, pyridine or the like usually under ice-cooling to at reflux temperature for 30 minutes to 1 day into Isocyanate compound (2).

Process 1-2

Urea compound (4) or a fused heterocyclic derivative of the present invention (Ia) can be prepared by allowing Isocyanate compound (2) and Amine compound (3) to react in an inert solvent such as tetrahydrofuran, methylene chloride, a mixed solvent thereof or the like in the presence or absence of a base such as triethylamine, N,N-diisopropylethylamine, pyridine, 4-dimethylaminopyridine or the like usually under ice-cooling to at reflux temperature for 1 hour to 3 days.

Process 1-3

A fused heterocyclic derivative of the present invention (Ia) also can be prepared by allowing Urea compound (4) to react in an inert solvent such as tetrahydrofuran, methylene chloride, methanol, ethanol, N,N-dimethylformamide, water, a mixed solvent thereof or the like in the presence or absence of a base such as triethylamine, N,N-diisopropylethylamine, pyridine, 4-dimethylaminopyridine, sodium methoxide, sodium ethoxide, sodium hydride, sodium hydroxide, lithium hydroxide or the like usually under ice-cooling to at reflux temperature for 5 minutes to 3 days.

[Method 2]

Among the fused heterocyclic derivatives represented by the general formula (I) of the present invention, a compound wherein E² is an oxygen atom can be prepared, for example, by Method 2.

[Chem. 15]

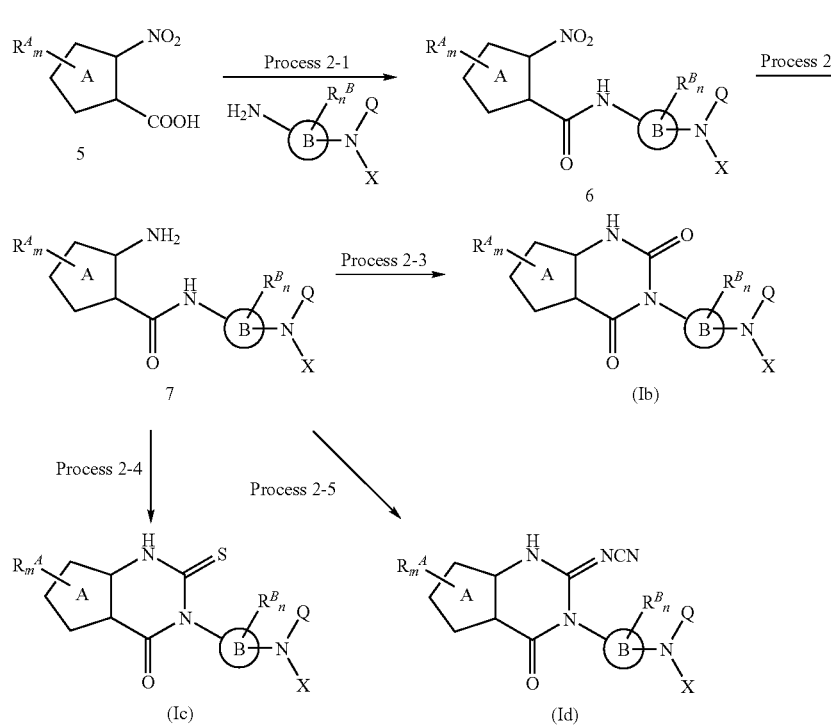

In the formula, ring A, ring B, $R^A$, $R^B$, m, n, Q and X have the same meanings as defined above.

Process 2-1

Amide compound (6) can be prepared by condensing Carboxylic acid compound (5) and Amine compound (3) by a general carboxylic chloride method or condensing agent method. A carboxylic chloride method can be conducted, for example, by treating Carboxylic acid compound (5) in an inert solvent such as methylene chloride, 1,2-dichloroethane, toluene, a mixed solvent thereof or the like using a reagent such as thionyl chloride, oxalyl chloride or the like in the presence or absence of an additive such as N,N-dimethylformamide or the like usually under ice-cooling to at reflux temperature for 30 minutes to 1 day to derive into the carboxylic chloride, and followed by allowing to react with Amine compound (3) in an inert solvent such as pyridine, methylene chloride, tetrahydrofuran, water, a mixed solvent thereof or the like in the presence or absence of a base such as triethylamine, N,N-diisopropylethylamine, pyridine, 4-dimethylaminopyridine, potassium carbonate, sodium hydrogen carbonate or the like usually under ice-cooling to at reflux temperature for 1 hour to 3 days. A condensing agent method can be conducted, for example, by allowing Carboxylic acid compound (5) and Amine compound (3) to react in an inert solvent such as N,N-dimethylformamide, methylene chloride, tetrahydrofuran, a mixed solvent thereof or the like using an condensing agent such as 1-ethyl-3-(3-dimethylaminopropyl)carbodiimide hydrochloride, dicyclohexylcarbodiimide or the like in the presence of an additive such as 1-hydroxybenzotriazole or the like in the presence or absence of a base such as triethylamine, N,N-diisopropylethylamine, pyridine, 4-dimethylaminopyridine or the like usually at from room temperature to reflux temperature for 1 hour to 3 days.

Process 2-2

Amine compound (7) can be prepared by reducing the nitro group of Amide compound (6) by a general catalytic reduction method, a metal hydride complex reduction method or the like. A catalytic reduction method can be conducted, for example, by treating Amide compound (6) under a hydrogen atmosphere in an inert solvent such as methanol, ethanol, ethyl acetate, tetrahydrofuran, acetic acid, a mixed solvent thereof or the like using a catalyst such as palladium-carbon powder or the like usually at from room temperature to reflux temperature for 1 hour to 3 days. A metal hydride complex reduction method can be conducted, for example, by treating Amide compound (6) in an inert solvent such as methanol, ethanol, tetrahydrofuran, a mixed solvent thereof or the like using a reducing agent such as sodium borohydride or the like in the presence of an additive such as nickel(II) bromide or the like usually under ice-cooling to at room temperature for 30 minutes to 1 day.

Process 2-3

A fused heterocyclic derivative of the present invention (Ib) can be prepared by treating Amine compound (7) in an inert solvent such as tetrahydrofuran, methylene chloride, N,N-dimethylformamide, a mixed solvent thereof or the like using a reagent such as phosgene, diphosgene, triphosgene, 1,1'-carbonylbis-1H-imidazole or the like in the presence or absence of a base such as triethylamine, N,N-diisopropylethylamine, pyridine, 4-dimethylamino-pyridine, sodium hydride or the like usually under ice-cooling to at reflux temperature for 30 minutes to 1 day.

Process 2-4

A fused heterocyclic derivative of the present invention (Ic) can be prepared by treating Amine compound (7) in an inert solvent such as tetrahydrofuran, N,N-dimethylformamide, methanol, ethanol, a mixed solvent thereof or the like using a reagent such as carbon disulfide or the like in the presence of a base such as triethylamine, N,N-diisopropylethylamine, sodium hydride, sodium hydroxide, potassium hydroxide or the like usually under ice-cooling to at reflux temperature for 1 hour to 3 days.

Process 2-5

A fused heterocyclic derivative of the present invention (Id) can be prepared by treating Amine compound (7) in an inert solvent such as tetrahydrofuran, N,N-dimethylformamide, methanol, ethanol, a mixed solvent thereof or the like using a reagent such as diphenylcyanocarbonimidate or the like in the presence of a base such as triethylamine, N,N-diisopropylethylamine, sodium hydride, sodium hydroxide, potassium hydroxide or the like usually under ice-cooling to at reflux temperature for 1 hour to 3 days.

[Method 3]

Amine compound (3) used as a starting material in the above Method 1 or 2 also can be obtained, for example, by reducing Nitro compound (8), which is commercially available or synthesized by a method described in literatures, combining general synthetic methods or the like, by a general reduction method or the like. For example, it can be prepared by the following Method 3.

[Chem. 16]

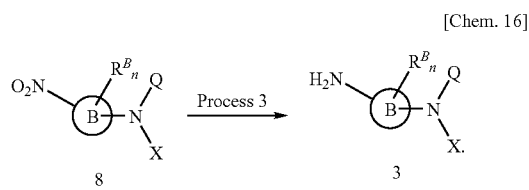

In the formula, ring B, $R^B$, n, Q and X have the same meanings as defined above.

Process 3

Amine compound (3) can be prepared by reducing Nitro compound (8) by a general catalytic reduction method, a metal hydride complex reduction method or the like. A catalytic reduction method can be conducted, for example, by treating Nitro compound (8) under a hydrogen atmosphere in an inert solvent such as methanol, ethanol, ethyl acetate, tetrahydrofuran, acetic acid, a mixed solvent thereof or the like using a catalyst such as palladium-carbon powder, rhodium-carbon powder, platinum-carbon powder or the like usually at from room temperature to reflux temperature for 1 hour to 3 days. A metal hydride complex reduction method can be conducted, for example, by treating Nitro compound (8) in an inert solvent such as methanol, ethanol, tetrahydrofuran, a mixed solvent thereof or the like using a reducing agent such as sodium borohydride or the like in the presence of an additive such as nickel(II) bromide or the like usually under ice-cooling to at room temperature for 30 minutes to 1 day.

In addition, when a compound used or prepared in the above Methods has a functional group which changes under the reaction conditions or inhibits the reaction progression, needless to say, the group may be protected by an appropriate protective group a commonly used by a skilled person in the art and the protective group may be removed in an appropriate step.

A fused heterocyclic derivative represented by the general formula (I) of the present invention can be converted into a prodrug wherein its carboxyl group, hydroxy group and/or amino group is converted, by allowing to react with a reagent to produce a prodrug. In addition, a prodrug of a fused heterocyclic derivative represented by the general formula (I) of the present invention may be a compound to be converted into a compound (1) of the present invention under physiological conditions described in "Iyakuhin no Kaihatsu" (Development of medicines), Vol. 7, Molecular design, pp. 163-198, issued by Hirokawa syoten (Hirokawa Book Store).

A fused heterocyclic derivative represented by the general formula (I) or a prodrug thereof can be converted into a pharmaceutically acceptable salt thereof in the usual way. As such a salt, for example, a salt with an inorganic acid such as hydrochloric acid, nitric acid or the like; a salt with an organic acid such as acetic acid, methanesulfonic acid or the like; and a sodium salt and a potassium salt; an additive salt with an organic base such as N,N'-dibenzylethylenediamine, 2-aminoethanol or the like can be illustrated.

A fused heterocyclic derivative represented by the general formula (I) or a prodrug thereof, or a pharmaceutically acceptable salt thereof sometimes can be obtained as a hydrate or solvate in the course of purification or preparing salts thereof. A fused heterocyclic derivative represented by the general formula (I) of the present invention or a prodrug thereof, or a pharmaceutically acceptable salt thereof includes a hydrate thereof or a solvate thereof with a pharmaceutically acceptable solvent. As the pharmaceutically acceptable solvent, ethanol or the like can be illustrated.

Furthermore, in a fused heterocyclic derivative represented by the general formula (I) or a prodrug thereof, there can be tautomers, geometrical isomers and/or optical isomers. For a pharmaceutical composition of the present invention, any of the isomers and a mixture thereof can be employed.

A fused heterocyclic derivative (I) of the present invention has an excellent GnRH antagonistic activity and can control the effect of gonadotropin releasing hormone and control the production and secretion of gonadotropin and sex hormones. As a result, a fused heterocyclic derivative (I) of the present invention or a prodrug thereof, or a pharmaceutically acceptable salt thereof is extremely useful as an agent for the prevention or treatment of sex hormone-dependent diseases such as benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor; a reproduction regulator, a contraceptive, an ovulation inducing agent or an agent for the prevention of post-operative recurrence of sex hormone-dependent cancers or the like.

A Pharmaceutical composition may be prepared by mixing a fused heterocyclic derivative (I) of the present invention or a prodrug thereof, or a pharmaceutically acceptable salt thereof, and a conventional pharmaceutical carrier.

The pharmaceutical carrier may be used optionally in combination according to a dosage form as described below. As the pharmaceutical carrier, for example, excipients such as lactose or the like; lubricants such as magnesium stearate or the like; disintegrators such as carboxymethylcellulose or the like; binders such as hydroxypropylmethylcellulose or the like; surfactants such as macrogol or the like; foamings such as sodium hydrogen carbonate or the like; dissolving aids such as cyclodextrin or the like; acidities such as citric acid or the like; stabilizers such as sodium edetate or the like; pH adjusters such as phosphoric acid salt or the like can be illustrated.

As the dosage form of the pharmaceutical composition of the present invention, for example, formulations for oral administration such as powders, granules, fine granules, dry syrups, tablets, capsules and the like; formulations for parenteral administration such as injections, poultices, suppositories and the like are illustrated, and a formulation for oral administration is preferable.

It is preferable to manufacture the above formulations in such a way that the dosage of the compound represented by the general formula (I) of the present invention or a pharmaceutically acceptable salt thereof is appropriately within the range of from 0.1 to 1,000 mg per day per adult human in case of oral administration and approximately within the range of from 0.01 to 100 mg per day per adult human in the case of parenteral injection in the formulation.

Furthermore, a pharmaceutical composition of the present invention can include other drug(s). Examples of such other drugs include a GnRH superagonist (for example, leuprorelin acetate, gonadorelin, buserelin, triptorelin, goserelin, nafarelin, histrelin, deslorelin, meterelin, lecirelin and the like), a chemotherapeutic agent (for example, ifosfamide, adriamycin, peplomycin, cisplatin, cyclophosphamide, 5-FU, UFT, methotrexate, mitomycin C, mitoxantrone, paclitaxel, dotaxel and the like), a peptidic GnRH antagonist (for example, cetrorelix, ganirelix, abarelix, ozarelix, iturelix, degarelix, teverelix and the like), a 5α-reductase inhibitor (for example, finasteride, dutasteride and the like), an α-adrenoceptor inhibitor (for example, tamsulosin, silodosin, urapidil and the like), an aromatase inhibitor (for example, fadrozole, letrozole, anastrozole, formestane and the like), an adrenal androgen production inhibitor (for example, liarozole and the like), a hormonotherapeutic agent (for example, an antiestrogenic agent such as tamoxifen, fulvestrant and the like, a progestational agent such as medroxyprogesterone and the like, an androgenic agent, an estrogenic agent and an antiandrogenic agent such as oxendolone, flutamide, nilutamide, bicalutamide and the like) and the like can be illustrated.

EXAMPLES

The present invention is further illustrated in more detail by way of the following Examples and Test Examples. However, the present invention is not limited thereto.

Reference Example 1

2,3-Difluoro-6-(2-methoxyethoxy)benzoic acid

To a suspension of 3,4-difluorophenol (2 g) and cesium carbonate (7.51 g) in N,N-dimethylformamide (15 mL) was added 2-methoxyethyl bromide (2.14 g), and the mixture was stirred at room temperature overnight. The reaction mixture was poured into water, and the resulting mixture was extracted with diethyl ether. The extract was washed with water twice and brine, and dried over anhydrous magnesium sulfate. The solvent was removed under reduced pressure, and the residue was purified by column chromatography on silica gel (eluent: n-hexane/ethyl acetate=5/1) to give 3,4-difluoro-1-(2-methoxyethoxy)-benzene (2.49 g). To the solution of the obtained 3,4-difluoro-1-(2-methoxyethoxy)benzene (1.47 g) in tetrahydrofuran (39 mL) was added n-butyllithium (2.64 mol/L n-hexane solution, 3.25 mL) at −78° C., and the mixture was stirred at the same temperature for 30 minutes. To the reaction mixture was added dry ice (10 g), and the mixture was stirred at the same temperature for 30 minutes, and then stirred at room temperature for 30 minutes. To the reaction mixture was added 2 mol/L hydrochloric acid, and the resulting mixture was extracted with ethyl acetate. The extract was washed with brine, and dried over anhydrous magnesium sulfate. The solvent was removed under reduced pressure to give the title compound (1.48 g).

Reference Example 2

2-Fluoro-5-{N-[2,3-difluoro-6-(2-methoxyethoxy)benzyl]-N-methylamino}aniline

To a solution of 2,3-difluoro-6-(2-methoxyethoxy)benzoic acid (0.5 g) in methylene chloride (7 mL) were added N,N-dimethylformamide (0.005 mL) and oxalyl chloride (0.75 mL), and the mixture was stirred at room temperature for 1 hour. The reaction mixture was concentrated under reduced pressure. To a suspension of 4-fluoro-3-nitroaniline (0.34 g) and sodium hydrogen carbonate (0.54 g) in tetrahydrofuran (5 mL) was added the solution of the residue in tetrahydrofuran (2 mL), and the mixture was stirred at room temperature overnight. The reaction mixture was poured into water, and the resulting mixture was extracted with ethyl acetate. The extract was washed with 1 mol/L hydrochloric acid, water and brine successively, and dried over anhydrous magnesium sulfate. The solvent was removed under reduced pressure, and the residue was purified by column chromatography on silica gel (eluent: n-hexane/ethyl acetate=½) to give 2,3-difluoro-6-(2-methoxyethoxy)-N-(4-fluoro-3-nitrophenyl)benzamide (0.59 g). This material was dissolved in N,N-dimethylformamide (10 mL). To the solution were added sodium hydride (55%, 77 mg) and methyl iodide (0.15 mL) under ice-cooling, and the mixture was stirred at room temperature for 2 hours. The reaction mixture was poured into water, and the resulting mixture was extracted with ethyl acetate. The extract was washed with water twice and brine, and dried over anhydrous magnesium sulfate. The solvent was removed under reduced pressure, and the residue was dissolved in methanol (5 mL)-tetrahydrofuran (5 mL). To the solution were added nickel(II) bromide (17 mg) and sodium borohydride (0.18 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/4) to give N-(3-amino-4-fluorophenyl)-2,3-difluoro-6-(2-methoxyethoxy)-N-methyl-benzamide (0.45 g). This material was dissolved in tetrahydrofuran (9.3 mL). To the solution was added borane-tetrahydrofuran complex (1.09 mol/L tetrahydrofuran solution, 3.5 mL), and the mixture was heated at reflux for 1 hour. To the reaction mixture was added methanol under ice-cooling, and the mixture was stirred for 10 minutes. The mixture was poured into a saturated aqueous sodium hydrogen carbonate solution, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane/ethyl acetate=1/1) to give the title compound (0.3 g).

Reference Examples 3 to 5

The compounds of Reference Examples 3 to 5 described in Table 1 were prepared in a similar manner to that described in Reference Example 2 using the corresponding starting materials.

Reference Example 6

6-(2-Acetyloxyethoxy)-2,3-difluorobenzyl bromide

To a suspension of 2,3-difluoro-6-hydroxybenzaldehyde (2.64 g) and potassium carbonate (3.47 g) in N,N-dimethylformamide (33 mL) were added 2-acetyloxyethyl bromide (2.03 mL) and sodium iodide (0.5 g), and the mixture was stirred at 60° C. overnight. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/1) to give 6-(2-acetyloxyethoxy)-2,3-difluorobenzaldehyde (3.35 g). This material was dissolved in tetrahydrofuran (27 mL). To the solution were added water (2.7 mL) and sodium borohydride (0.52 g) under ice-cooling, and the mixture was stirred at the same temperature for 5 minutes, and then stirred at room temperature for 1 hour. The reaction mixture was diluted with water, and the resulting mixture was extracted with ethyl acetate. The extract was washed with brine, and dried over anhydrous magnesium sulfate. The solvent was removed under reduced pressure to give 6-(2-acetyloxyethoxy)-2,3-difluorobenzyl alcohol (3.2 g). To the solution of the obtained 6-(2-acetyloxyethoxy)-2,3-difluorobenzyl alcohol (1.81 g) and triethylamine (0.97 g) in ethyl acetate (25 mL) was added methanesulfonyl chloride (0.63 mL) under ice-cooling, and the mixture was stirred at the same temperature for 30 minutes. The insoluble material was removed by filtration, and the insoluble material was washed with ethyl acetate (15 mL). The filtrate and washing were combined. To the solution was added lithium bromide (1.92 g), and the mixture was stirred at 60° C. for 1 hour. The reaction mixture was poured into water, and the organic layer was separated. The organic layer was washed with water and brine, and dried over anhydrous magnesium sulfate. The solvent was removed under reduced pressure to give the title compound (2.12 g).

Reference Example 7

The compound of Reference Example 7 described in Table 1 was prepared in a similar manner to that described in Reference Example 6 using the corresponding starting materials.

Reference Example 8

4-Fluoro-2-methoxy-5-nitroaniline

To a suspension of 4-fluoro-2-methoxyaniline (0.71 g) in concentrated sulfuric acid (7.5 mL) was added guanidine nitrate (0.61 g) under ice-cooling over 15 minutes, and the mixture was stirred at the same temperature for 15 minutes. The reaction mixture was poured into a saturated aqueous sodium hydrogen carbonate solution cooled in ice, and the precipitated crystals were collected by filtration. The crystals were dissolved in ethyl acetate, and the solution was dried over anhydrous magnesium sulfate. The solvent was removed under reduced pressure to give the title compound (0.78 g).

Reference Example 9

2-Fluoro-5-[N-(2,3-difluoro-6-methoxybenzyl)-N-methylamino]-4-methoxyaniline To a suspension of 4-fluoro-2-methoxy-5-nitroaniline (0.37 g) and potassium carbonate (0.36 g) in N,N-dimethylformamide (10 mL) was added 2,3-difluoro-6-methoxybenzyl-bromide (0.47 g), and the mixture was stirred at room temperature for 3 hours. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=4/1) to give 5-fluoro-2-(2,3-difluoro-6-methoxybenzylamino)-4-nitroanisole (0.32 g). This material was dissolved in N,N-dimethylformamide (9.3 mL). To the solution were added sodium hydride (55%, 45 mg) and methyl iodide (0.18 mL) under ice-cooling, and the mixture was stirred at room temperature overnight. The reaction mixture was poured into water, and the resulting mixture was extracted with ethyl acetate. The extract was washed with water twice and brine, and dried over anhydrous magnesium sulfate. The solvent was removed under reduced pressure, and the residue was dissolved in methanol (4 mL)-tetrahydrofuran (4 mL). To the solution were added nickel(II) bromide (11 mg) and sodium borohydride (0.11 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/1) to give the title compound (0.17 g).

Reference Examples 10 to 12

The compounds of Reference Examples 10 to 12 described in Table 2 were prepared in a similar manner to that described in Reference Example 9 using the corresponding starting materials.

Reference Example 13

2-Fluoro-5-[N-(2,3-difluoro-6-methoxybenzyl)—N-methanesulfonylamino]-4-methoxyaniline To a solution of 4-fluoro-2-methoxy-5-nitroaniline (0.16 g) and pyridine (0.21 mL) in tetrahydrofuran (3 mL) was added methanesulfonyl chloride (0.074 mL) under ice-cooling, and the mixture was stirred at room temperature for 3 hours, and then stirred at 50° C. overnight. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/3) to give 5-fluoro-2-methanesulfonylamino-4-nitroanisole (0.1 g). This material was dissolved in N,N-dimethylformamide (3 mL). To the solution were added potassium carbonate (68 mg) and 2,3-difluoro-6-methoxybenzyl bromide (99 mg), and the mixture was stirred at room temperature for 2 hours. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=½) to give 5-fluoro-2-[N-(2,3-difluoro-6- methoxybenzyl)-N-methanesulfonylamino]-4-nitroanisole (0.14 g). This material was dissolved in tetrahydrofuran (2 mL). To the solution was added 10% palladium-carbon powder (13 mg), and the mixture was stirred at room temperature under a hydrogen atmosphere overnight. The insoluble material was removed by filtration, and the filtrate was concentrated under reduced pressure. The residue was purified by column chromatography on silica gel (eluent: n-hexane/ethyl acetate=½) to give the title compound (80 mg).

Reference Examples 14 to 18

The compounds of Reference Examples 14 to 18 described in Tables 2 and 3 were prepared in a similar manner to that described in Reference Example 13 using the corresponding starting materials.

Example 1

5-Carboxy-3-(2-fluoro-5-{N-[2,3-difluoro-6-(2-methoxyethoxy)benzyl]-N-methylamino}-phenyl) thieno[3,4-d]pyrimidine-2,4(1H,3H)-dione To a suspension of dimethyl 4-aminothiophene-2,3-dicarboxylate hydrochloride (0.15 g) and triethylamine (0.23 mL) in tetrahydrofuran (4 mL) was added a solution of triphosgene (0.11 g) in tetrahydrofuran (4 mL) under ice-cooling, and the mixture was stirred at 60° C. for 30 minutes. The reaction mixture was diluted with ethyl acetate, and the insoluble material was removed by filtration. The filtrate was concentrated under reduced pressure, and the residue was dissolved in tetrahydrofuran (4 mL). To a solution of 2-fluoro-5-{N-[2, 3-difluoro-6-(2-methoxyethoxy)benzyl]-N-methylamino}aniline (0.18 g) and 4-dimethylaminopyridine (0.2 g) in tetrahydrofuran (4 mL) was added the solution, and the mixture was stirred at 60° C. overnight. The reaction mixture was passed through VARIAN BOND ELUT-SCX, and eluted with ethyl acetate. The eluate was concentrated under reduced pressure, and the residue was dissolved in methanol (5 mL). To the solution was added sodium methoxide (28% methanol solution, 0.32 mL), and the mixture was stirred at room temperature for 10 minutes. To the reaction mixture was added 1 mol/L hydrochloric acid, and the resulting mixture was extracted with ethyl acetate. The extract was washed with water and brine, and dried over anhydrous magnesium sulfate. The solvent was removed under reduced pressure. The mixture of the residue and lithium hydroxide monohydrate (0.15 g) in methanol (3 mL) was stirred at 50° C. for 30 minutes. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: ethyl acetate) to give the title compound (0.13 g).

Examples 2 to 14

The compounds of Examples 2 to 14 described in Tables 4 and 5 were prepared in a similar manner to that described in Example 1 using the corresponding starting materials.

Tables 1 to 3 and Tables 4 to 5 show the chemical structure and $^1$H-NMR data of the above compounds of Reference Examples 1 to 18 and Examples 1 to 14, respectively.

The abbreviations in these Tables: "Ref No.", "Ex No.", "Strc" and "Solv", represent Reference Example number, Example number, chemical structure and measurement solvent of $^1$H-NMR, respectively.

TABLE 1

| Ref No. | Strc | (Solv) $^1$H-NMR δ ppm: |
|---|---|---|
| 1 | 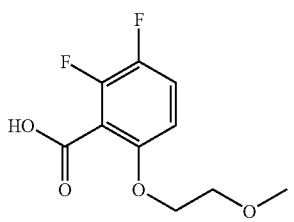 [SMILES: COCCOc1ccc(F)c(F)c1C(=O)O] | (CDCl3) 3.45 (3H, s), 3.75-3.8 (2H, m), 4.25-4.3 (2H, m), 6.7-6.8 (1H, m), 7.2-7.35 (1H, m) |
| 2 | 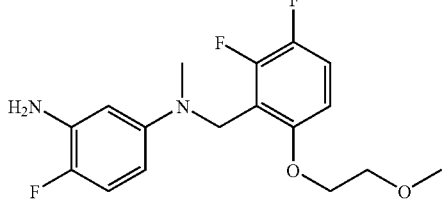 | (CDCl3) 2.8-2.85 (3H, m), 3.44 (3H, s), 3.7-3.8 (4H, m), 4.05-4.15 (2H, m), 4.4-4.45 (2H, m), 6.15-6.25 (1H, m), 6.45-6.6 (2H, m), 6.82 (1H, dd, J = 10.7 Hz, 8.8 Hz), 6.95-7.05 (1H, m) |
| 3 | 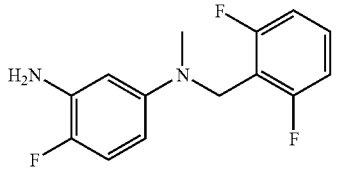 [SMILES: CN(Cc1c(F)cccc1F)c1ccc(F)c(N)c1] | (CDCl3) 2.81 (3H, s), 3.63 (2H, brs), 4.41 (2H, s), 6.2-6.3 (1H, m), 6.34 (1H, dd, J = 7.8 Hz, 3.1 Hz), 6.8-6.95 (3H, m), 7.15-7.3 (1H, m) |

TABLE 1-continued

| Ref No. | Strc | (Solv) ¹H-NMR δ ppm: |
|---|---|---|
| 4 | | (CDCl3) 1.06 (3H, t, J = 7.0 Hz), 3.25 (2H, q, J = 7.0 Hz), 3.6 (2H, brs), 3.79 (3H, s), 4.35-4.4 (2H, m), 6.15-6.25 (1H, m), 6.32 (1H, dd, J = 7.9 Hz, 2.8 Hz), 6.5-6.6 (1H, m), 6.82 (1H, dd, J = 10.8 Hz, 8.7 Hz), 6.95-7.1 (1H, m) |
| 5 | | (CDCl3) 3.31 (3H, s), 3.4-3.5 (4H, m), 3.6 (2H, brs), 3.79 (3H, s), 4.45-4.5 (2H, m), 6.15-6.2 (1H, m), 6.3 (1H, dd, J = 7.6 Hz, 3.2 Hz), 6.5-6.6 (1H, m), 6.81 (1H, dd, J = 10.8 Hz, 8.7 Hz), 6.95-7.05 (1H, m) |
| 6 | | (CDCl3) 2.12 (3H, s), 4.2-4.25 (2H, m), 4.45-4.5 (2H, m), 4.55-4.6 (2H, m), 6.55-6.6 (1H, m), 7.0-7.15 (1H, m) |
| 7 | | (CDCl3) 3.47 (3H, s), 3.75-3.85 (2H, m), 4.15-4.2 (2H, m), 4.55-4.6 (2H, m), 6.55-6.65 (1H, m), 7.0-7.1 (1H, m) |

TABLE 2

| Ref No. | Strc | (Solv) ¹H-NMR δ ppm: |
|---|---|---|
| 8 | | (CDCl3) 3.8-4.0 (5H, m), 6.64 (1H, d, J = 12.3 Hz), 7.4 (1H, d, J = 7.3 Hz) |
| 9 | | (CDCl3) 2.6-2.65 (3H, m), 3.29 (2H, brs), 3.52 (3H, s), 3.85 (3H, s), 4.4-4.45 (2H, m), 6.19 (1H, d, J = 9.2 Hz), 6.4-6.5 (1H, m), 6.6 (1H, d, J = 12.3 Hz), 6.9-7.05 (1H, m) |

TABLE 2-continued

| Ref No. | Strc | (Solv) $^1$H-NMR δ ppm: |
|---|---|---|
| 10 | | (CDCl3) 2.75-2.8 (3H, m), 3.62 (2H, brs), 3.79 (3H, s), 4.35-4.4 (2H, m), 6.2-6.3 (1H, m), 6.36 (1H, dd, J = 7.7 Hz, 3.0 Hz), 6.5-6.6 (1H, m), 6.84 (1H, dd, J = 10.8 Hz, 8.9 Hz), 6.95-7.1 (1H, m) |
| 11 | | (CDCl3) 1.07 (3H, t, J = 7.0 Hz), 3.27 (2H, q, J = 7.0 Hz), 3.62 (2H, brs), 4.39 (2H, s), 6.15-6.25 (1H, m), 6.32 (1H, dd, J = 7.8 Hz, 3.1 Hz), 6.8-6.95 (3H, m), 7.15-7.25 (1H, m) |
| 12 | | (CDCl3) 2.08 (3H, s), 2.75-2.8 (3H, m), 3.69 (2H, brs), 4.1-4.2 (2H, m), 4.35-4.45 (4H, m), 6.2-6.3 (1H, m), 6.42 (1H, dd, J = 7.6 Hz, 2.8 Hz), 6.5-6.6 (1H, m), 6.83 (1H, dd, J = 10.7 Hz, 9.2 Hz), 7.0-7.1 (1H, m) |
| 13 | | (CDCl3) 3.02 (3H, s), 3.33 (2H, brs), 3.68 (3H, s), 3.69 (3H, s), 4.88 (2H, s), 6.4-6.5 (1H, m), 6.5-6.6 (2H, m), 6.95-7.05 (1H, m) |
| 14 | | (CDCl3) 3.0 (3H, s), 3.65-3.75 (5H, m), 4.87 (2H, s), 6.4-6.55 (2H, m), 6.6-6.7 (1H, m), 6.8-6.9 (1H, m), 6.95-7.05 (1H, m) |

TABLE 3

| Ref No. | Strc | (Solv) $^1$H-NMR δ ppm: |
|---|---|---|
| 15 | | (DMSO-d6) 1.73 (3H, s), 3.63 (3H, s), 4.84 (2H, s), 5.21 (2H, s), 6.1-6.2 (1H, m), 6.4-6.5 (1H, m), 6.65-6.75 (1H, m), 6.8-6.95 (1H, m), 7.2-7.3 (1H, m) |

TABLE 3-continued

| Ref No. | Strc | (Solv) ¹H-NMR δ ppm: |
|---|---|---|
| 16 | | (CDCl3) 3.01 (3H, s), 3.47 (3H, s), 3.7-3.85 (4H, m), 3.95-4.05 (2H, m), 4.91 (2H, s), 6.4-6.5 (2H, m), 6.7-6.85 (2H, m), 6.9-7.05 (1H, m) |
| 17 | | (CDCl3) 1.88 (3H, s), 3.46 (3H, s), 3.65-3.85 (4H, m), 3.9-4.0 (2H, m), 5.03 (2H, s), 6.25-6.35 (1H, m), 6.35-6.45 (1H, m), 6.56 (1H, dd, J = 8.2 Hz, 2.5 Hz), 6.77 (1H, dd, J = 10.7 Hz, 8.5 Hz), 6.85-7.0 (1H, m) |
| 18 | | (CDCl3) 3.5-3.8 (8H, m), 4.9-4.95 (2H, m), 6.3-6.55 (3H, m), 6.82 (1H, dd, J = 10.7 Hz, 8.8 Hz), 6.9-7.05 (1H, m) |

TABLE 4

| Ex No. | Strc | (Solv) ¹H-NMR δ ppm: |
|---|---|---|
| 1 | | (DMSO-d6) 2.82 (3H, s), 3.23 (3H, s), 3.55-3.65 (2H, m), 4.05-4.15 (2H, m), 4.45-4.55 (2H, m), 6.8-6.9 (1H, m), 6.9-7.05 (2H, m), 7.15-7.25 (1H, m), 7.25-7.4 (2H, m), 11.99 (1H, s), 14.52 (1H, s) |
| 2 | | (DMSO-d6) 2.79 (3H, s), 4.53 (2H, s), 6.9-7.0 (2H, m), 7.05-7.15 (2H, m), 7.2-7.3 (1H, m), 7.35-7.45 (2H, m), 11.97 (1H, s), 14.52 (1H, s) |
| 3 | | (DMSO-d6) 2.76 (3H, s), 3.77 (3H, s), 4.48 (2H, s), 6.8-6.9 (1H, m), 6.9-7.0 (2H, m), 7.15-7.25 (1H, m), 7.3-7.4 (2H, m), 11.98 (1H, s), 14.53 (1H, s) |

TABLE 4-continued

| Ex No. | Strc | (Solv) ¹H-NMR δ ppm: |
|---|---|---|
| 4 | | (DMSO-d6) 1.0 (3H, t, J = 7.0 Hz), 3.26 (2H, q, J = 7.0 Hz), 4.45-4.55 (2H, m), 6.9-7.0 (2H, m), 7.05-7.25 (3H, m), 7.35-7.5 (2H, m), 11.99 (1H, s), 14.55 (1H, brs) |
| 5 | | (DMSO-d6) 3.1 (3H, s), 3.63 (3H, s), 4.75-4.9 (2H, m), 6.7-6.75 (1H, m), 7.25-7.35 (1H, m), 7.35-7.5 (4H, m), 12.01 (1H, s), 14.4 (1H, brs) |
| 6 | | (DMSO-d6) 1.76 (3H, s), 3.58 (3H, s), 4.8-5.0 (2H, m), 6.65-6.75 (1H, m), 7.2-7.45 (5H, m), 11.99 (1H, s), 14.39 (1H, s) |
| 7 | | (DMSO-d6) 3.12 (3H, s), 3.23 (3H, s), 3.5-3.6 (2H, m), 3.99 (2H, t, J = 4.6 Hz), 4.8-4.9 (2H, m), 6.7-6.8 (1H, m), 7.2-7.3 (1H, m), 7.35-7.5 (4H, m), 12.01 (1H, s), 14.38 (1H, s) |
| 8 | | (DMSO-d6) 1.77 (3H, s), 3.24 (3H, s), 3.45-3.6 (2H, m), 3.9-4.0 (2H, m), 4.85-5.0 (2H, m), 6.65-6.75 (1H, m), 7.15-7.45 (5H, m), 12.01 (1H, s), 14.37 (1H, s) |

TABLE 5

| Ex No. | Strc | (Solv) ¹H-NMR δ ppm: |
|---|---|---|
| 9 | | (DMSO-d6) 2.83 (3H, s), 3.6-3.7 (2H, m), 3.95-4.05 (2H, m), 4.45-4.6 (2H, m), 4.8-5.0 (1H, m), 6.8-6.9 (1H, m), 6.95-7.05 (2H, m), 7.15-7.25 (1H, m), 7.25-7.4 (2H, m), 11.99 (1H, s), 14.56 (1H, brs) |

TABLE 5-continued

| Ex No. | Strc | (Solv) $^1$H-NMR δ ppm: |
|---|---|---|
| 10 | 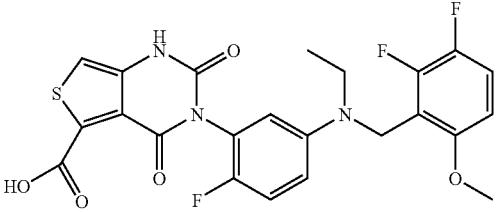 [SMILES: CCN(Cc1c(OC)ccc(F)c1F)c1ccc(F)c(-n2c(=O)[nH]c3csc(C(=O)O)c3c2=O)c1] | (DMSO-d6) 0.99 (3H, t, J = 6.9 Hz), 3.24 (2H, q, J = 6.9 Hz), 3.79 (3H, s), 4.44 (2H, s), 6.8-7.0 (3H, m), 7.15-7.25 (1H, m), 7.3-7.4 (2H, m), 11.99 (1H, s), 14.57 (1H, s) |
| 11 | 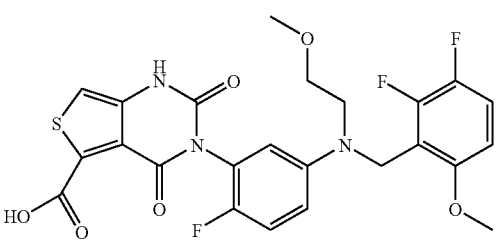 [SMILES: COCCN(Cc1c(OC)ccc(F)c1F)c1ccc(F)c(-n2c(=O)[nH]c3csc(C(=O)O)c3c2=O)c1] | (DMSO-d6) 3.2 (3H, s), 3.35-3.45 (4H, m), 3.79 (3H, s), 4.51 (2H, s), 6.8-7.0 (3H, m), 7.15-7.25 (1H, m), 7.3-7.4 (2H, m), 11.99 (1H, s), 14.55 (1H, s) |
| 12 | 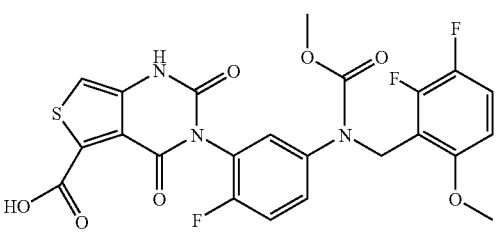 [SMILES: COC(=O)N(Cc1c(OC)ccc(F)c1F)c1ccc(F)c(-n2c(=O)[nH]c3csc(C(=O)O)c3c2=O)c1] | (DMSO-d6) 3.61 (3H, s), 3.62 (3H, s), 4.8-4.95 (2H, m), 6.65-6.75 (1H, m), 7.2-7.4 (5H, m), 12.01 (1H, s), 14.43 (1H, s) |
| 13 | 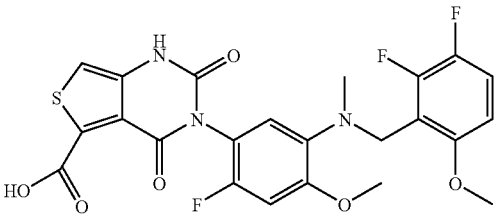 [SMILES: COc1cc(F)c(-n2c(=O)[nH]c3csc(C(=O)O)c3c2=O)cc1N(C)Cc1c(OC)ccc(F)c1F] | (DMSO-d6) 3.32 (3H, s), 3.8 (3H, s), 3.83 (3H, s), 4.15-4.25 (2H, m), 6.79 (1H, d, J = 7.2 Hz), 6.8-6.9 (1H, m), 6.96 (1H, d, J = 11.5 Hz), 7.3-7.4 (2H, m), 11.98 (1H, s), 14.65 (1H, s) |
| 14 | 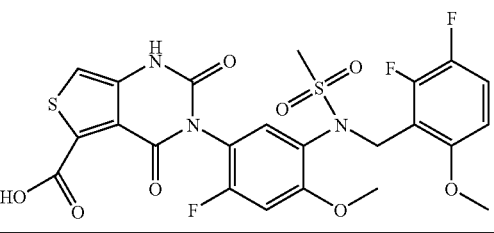 | (DMSO-d6) 3.08 (3H, s), 3.61 (3H, s), 3.87 (3H, s), 4.55-4.95 (2H, m), 6.65-6.75 (1H, m), 7.05-7.4 (4H, m), 11.94 (1H, s), 14.55 (1H, s) |

Test Example 1

1) Cloning and Construction of the Vector Expressing Human GnRH Receptor1 (GnRHR1)

Using cDNA derived from human pituitary (BECTON DICKINSON) as a template, the DNA fragment coding 45 to 1115 by of human GnRHR1 (Accession No. L03380), which was reported by Kakar et al., was amplified by PCR method and inserted into the multi-cloning site of pcDNA3.1(+) (Invitrogen). The DNA sequence inserted was perfectly matched to the previously reported sequence.

2) Establishment of Cell Line Stably Expressing Human GnRH Receptor1 HEK293 Cells The expression vector of human GnRHR1 gene, was digested by XhoI into a linear DNA. The linear DNA was transfected into HEK293 cells by means of lipofection (Lipofectamine2000: Invitrogen). Neomycin resistant cell lines were selected by culture in the medium containing G418 (Invitrogen) at 1 mg/mL, and then the change of calcium levels in GnRH-stimulated cells was measured by the method described below. The cell line, which showed the greatest change, was selected and designated as hGnRHR1#1. hGnRHR1#1 cells were cultured in the presence of G418 at 0.5 mg/mL.

3) Assay of Inhibitory Effect for the Change of Calcium Levels in GnRH-Stimulated Cells Antagonizing effect of compounds for human GnRHR1 was evaluated by depression of calcium levels in GnRH-stimulated cells. hGnRHR1#1 cells were seeded into a 96-well culture plate at a density of $1.5 \times 10^5$ cells/well and cultured for a day. After removing the culture medium, cells were washed with 200 μL per well of the washing buffer (Hanks' Balanced Salt Solutions, 20 mM N-2-hydroxyethylpiperazine-N'-2-ethanesulfonic acid, 1.3 mM calcium chloride, 0.5 mM magnesium chloride, 0.4 mM magnesium sulfate). One hundred μL of the $Ca^{2+}$ sensitive dye solution (FLIPR Calcium Assay Kit, Molecular Devices) was added to the well, and the cells were incubated for 1 hour at 37° C. in 5% $CO_2$ incubator. Then, intracellular calcium levels were determined under the following condition by using FLEX STATION (Molecular Devices). In the equipment, which was warmed to 37° C., 50 μL of test compound diluted with the measurement buffer (the washing buffer with 0.1% Albumin bovine serum) was added to the well. After 1 minute, 50 μL of 10 nM GnRH was added to the well. The drug concentration, at which 50% GnRH-stimulated intracellular calcium flux was inhibited ($IC_{50}$ value), was calculated using logit plot (Table 6).

TABLE 6

| Example No. | $IC_{50}$ (nM) |
| --- | --- |
| 1 | 51 |
| 2 | 133 |
| Control compound 1 | 18 |

Test Example 2

Assay for Oral Absorbability

1) Preparation of the Samples for Measurement of the Drug Concentration after Oral Administration As experimental animal, overnight fasted SD rats (Charles River, male, 7 weeks of age, 170-210 g) were used. Three mg of a test compound was dissolved by adding 0.2 mL of N,N-dimethylacetoamide, 9.794 mL of 0.5% aqueous methylcellulose solution and 0.006 mL of 2N NaOH, and then 0.3 mg/mL solution was prepared. The body weights of rats were measured, and the solution of the test compound was administered orally at the dose of 10 mL/kg (3 mg/kg). The oral administration was performed with gastric tube for rat and 2.5 mL syringe. The sampling times for collection of blood were 15, 30, 60, 120, 240 and 360 minutes after the oral administration. The blood was centrifuged, and the plasma was used as the sample for measurement of the drug concentration in blood.

2) Measurement of the Drug Concentration

To 0.025 mL of the plasma obtained in 1) described above, 0.1 mL of an adequate internal standard material was added according to the usual method, and then deproteinization was performed by adding 0.875 mL of acetonitrile. After centrifugation, 0.005 mL of the supernatant was injected into LC-MS/MS. The drug concentration in plasma was measured by LC-MS/MS method under the conditions as follows. To 0.05 mL of the blank plasma were added the internal standard material and various test compounds adequately according to the usual method, similar operating described above was done, and then the standard curves were prepared.

LC

Instrument: Agilent1100

Column: Cadenza C18 3 μm 4.6×50 mm

Mobile phase: 10 mM aqueous ammonium acetate solution (pH 4.5) (A)/acetonitrile (B)(Time and ratio of (A)/(B) are shown in Table 7.)

Column temperature: 40° C.

Flow rate: 0.5 mL/min

MS/MS

Instrument: API-4000

Ionization method: ESI (Turbo Ion Spray)

TABLE 7

| Time (min) | A (%) | B (%) |
| --- | --- | --- |
| 0.0 | 90 | 10 |
| 3.0 | 90 | 10 |
| 4.0 | 10 | 90 |
| 7.0 | 10 | 90 |
| 7.1 | 90 | 10 |
| 12.0 | 90 | 10 |

In the oral administration, the maximum plasma drug concentration ($C_{max}$) and the plasma drug concentration at 360 minutes after administration ($C_{360}$) are shown in Tables 8 and 9, respectively.

TABLE 8

| Test compound | Cmax (ng/mL) |
| --- | --- |
| Example 1 | 17608 |
| Example 2 | 14939 |
| Control compound 1 | 342 |

TABLE 9

| Test compound | $C_{360}$ |
| --- | --- |
| Example 1 | 1010 |
| Example 2 | 2168 |
| Control compound 1 | 21 |

In Tables 6, 8 and 9, Control compound 1 is the sulfonamide compound of Example 15 described in the above Patent reference 3.

As shown above, a fused heterocyclic derivative of the present invention is more superior in blood kinetics such as availability and sustainability by oral administration than the Control compound. For example, the fused heterocyclic derivatives of Examples 1 and 2 exert more excellent availability than the Control compound 1, and thus, is more preferable as a pharmaceutical composition for oral administration. In addition, the fused heterocyclic derivatives of Examples 1 and 2 maintain their blood concentrations 6 hours after the oral administrations and more superior in sustainability than the Control compound. Therefore, the fused heterocyclic derivatives of the present invention can be used as a long-acting preparation substantially without a sustained-release base such as hydroxyalkylcellulose, alkylcellulose or the like.

Industrial Applicability

A fused heterocyclic derivative (I) of the present invention or a prodrug thereof, or a pharmaceutically acceptable salt thereof has an excellent GnRH antagonistic activity, and thus, can be used as an agent for the prevention or treatment of sex hormone-dependent diseases by controlling the effect of gonadotropin releasing hormone and controlling the production and secretion of gonadotropin and sex hormones. Therefore, the present invention can provide an agent for the prevention or treatment of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer or pituitary tumor, a reproduction regulator, a contraceptive, an ovulation inducing agent or an agent for the prevention of post-operative recurrence of sex hormone-dependent cancers and the like.

The invention claimed is:

1. A fused heterocyclic compound represented by the formula (I):

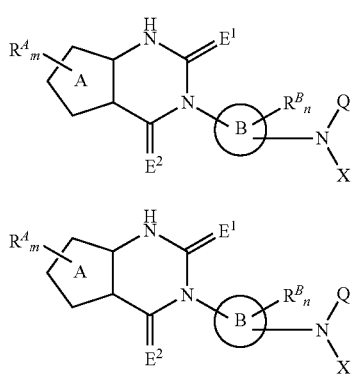

wherein ring A represents a thiophene ring represented by the following formula:

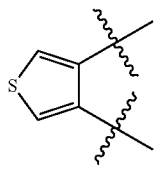 [SMILES: *c1cscc1*]

$R^A$ represents a halogen atom, a lower alkyl group which may have any substituent selected from substituent group (A-1), —COOW$^1$ or —CONW$^2$W$^3$, in which W$^1$, W$^2$ and W$^3$ independently represent a hydrogen atom or a lower alkyl group which may have any substituent selected from substituent group (A-1), or W$^2$ and W$^3$ optionally bind together to form a cyclic amino group which may have any substituent selected from substituent group (B-1) with the neighboring nitrogen atom;

m represents an integer number 0 or 1;

ring B represents a benzene ring, a thiophene ring or a pyridine ring;

$R^B$ represents a halogen atom, a lower alkyl group optionally substituted by a halogen atom, or —OW$^4$ in which W$^4$ represent a hydrogen atom or a lower alkyl group which may have any substituent selected from substituent group (A-2);

n represents an integer number 0 to 2;

E$^1$ represents an oxygen atom;

E$^2$ represents an oxygen atom;

Q represents a hydrogen atom, a lower alkyl group which may have any substituent selected from substituent group (A-2), —COW$^7$ or —SO$_2$W$^8$;

X represents a group represented by -L-Z, in which W$^7$ represents a lower alkyl group which may have any substituent selected from substituent group (A-2) or a lower alkoxy group which may have any substituent selected from substituent group (A-2);

W$^8$ represents a lower alkyl group which may have any substituent selected from substituent group (A-2);

L represents a lower alkylene group which may have any substituent selected from substituent group (A-2);

Z represents an optionally fused aryl group which may have any substituent selected from substituent group (C);

and with the proviso that when Z is aryl which may have any substituent selected from substituent group (C), the aryl has at least one substituent;

substituent group (A-1): a halogen atom, a cyano group, a hydroxy group, a lower alkoxy group, a (lower alkyl) thio group, an amino group, a (di)(lower alkyl)amino group, a carboxy group, a (lower alkoxy)carbonyl group, a carbamoyl group and a (di)(lower alkyl)carbamoyl group;

substituent group (A-2): a halogen atom, a cyano group, a hydroxy group, a lower alkoxy group, a (lower alkyl) thio group, an amino group, a (di)(lower alkyl)amino group, a carboxy group, a (lower alkoxy)carbonyl group, a carbamoyl group, a (di)(lower alkyl)carbamoyl group, an aryl group and a heteroaryl group;

substituent group (B-1): an oxo group, a halogen atom, a cyano group, a hydroxy group, a lower alkyl group which may have any substituent selected from substituent group (A-1), a cycloalkyl group, a lower alkoxy group which may have any substituent selected from substituent group (A-1), a (lower alkyl)thio group which may have any substituent selected from substituent group (A-1), a carboxy group, a (lower alkoxy)carbonyl group which may have any substituent selected from substituent group (A-1), a carbamoyl group, a (di)(lower alkyl)carbamoyl group and an acylamino group;

substituent group (C): a halogen atom, a nitro group, a cyano group, a hydroxy group, a lower alkyl group which may have any substituent selected from substituent group (A-2), a cycloalkyl group, a lower alkoxy group which may have any substituent selected from substituent group (A-2), a (lower alkyl)thio group which may have any substituent selected from substituent group (A-2), a carboxy group, a (lower alkoxy)carbonyl group which may have any substituent selected from substituent group (A-2), a carbamoyl group, a (di)(lower alkyl)carbamoyl group, an aryl group, an aryloxy group, a heteroaryl group, a heteroaryloxy group and an acylamino group; or a pharmaceutically acceptable salt thereof.

2. A fused heterocyclic compound as claimed in claim 1, wherein $R^A$ is a lower alkyl group substituted by a group selected from the group consisting of a hydroxy group, a carboxy group and a carbamoyl group; a carboxy group; or a carbamoyl group, or a pharmaceutically acceptable salt thereof.

3. A fused heterocyclic compound as claimed in claim 1, wherein m is 1 and ring A having $R^A$ on the ring is represented by the following formula:

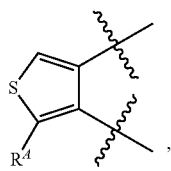

or a pharmaceutically acceptable salt thereof.

4. A fused heterocyclic compound as claimed in claim 1, wherein ring B is any of rings represented by the formula:

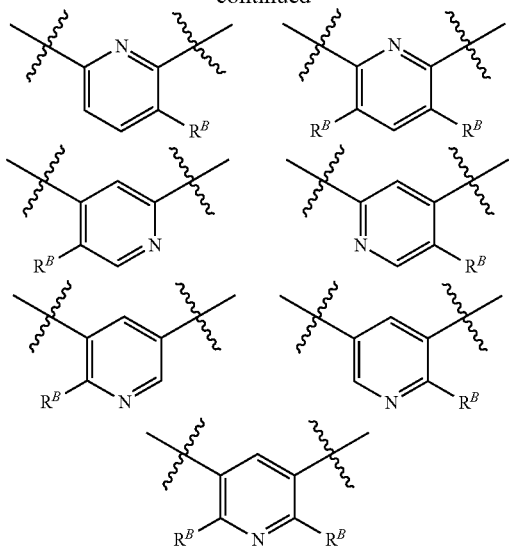

or a pharmaceutically acceptable salt thereof.

5. A fused heterocyclic compound as claimed in claim 4, wherein n is 1 or 2 and ring B having $R^B$ on the ring is any of benzene rings, pyridine rings and thiophene rings represented by the following formula:

in the formula, and when two $R^B$ exist, these two $R^B$ may be the same or different from each other, or a pharmaceutically acceptable salt thereof.

6. A fused heterocyclic compound as claimed in claim 4, wherein ring B is any of rings represented by the formula:

or a pharmaceutically acceptable salt thereof.

7. A fused heterocyclic compound as claimed in claim 1, wherein $R^B$ is a fluorine atom, a chlorine atom or —$OW^4$ in which $W^4$ is a lower alkyl group, or a pharmaceutically acceptable salt thereof.

8. A fused heterocyclic compound as claimed in claim 1, wherein Q is a lower alkyl group which may have any substituent selected from substituent group (A-2), or a pharmaceutically acceptable salt thereof.

9. A fused heterocyclic compound as claimed in any of claims 1, wherein L is a $C_{1-3}$ alkylene group, or a pharmaceutically acceptable salt thereof.

10. A pharmaceutical composition comprising as an active ingredient a fused heterocyclic compound as claimed in claim 1, or a pharmaceutically acceptable salt thereof.

\* \* \* \* \*

UNITED STATES PATENT AND TRADEMARK OFFICE
CERTIFICATE OF CORRECTION

PATENT NO. : 8,426,427 B2
APPLICATION NO. : 12/595931
DATED : April 23, 2013
INVENTOR(S) : Kohsuke Ohno and Moboru Kamada It is certified that error appears in the above-identified patent and that said Letters Patent is hereby corrected as shown below:

In the Claims: Column 37, Line 21 delete duplicate Formula (I).

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,426,427 B2 | |
| APPLICATION NO. | : 12/595931 | |
| DATED | : April 23, 2013 | |
| INVENTOR(S) | : Kohsuke Ohno and Moboru Kamada | |

It is certified that error appears in the above-identified patent and that said Letters Patent is hereby corrected as shown below:

In the Claims: Column 37, Line 21 delete duplicate Formula (I).

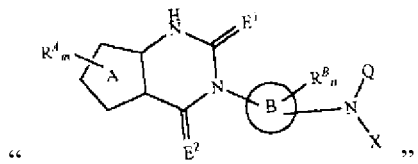

This certificate supersedes the Certificate of Correction issued July 30, 2013.

Signed and Sealed this
Seventh Day of January, 2014

Margaret A. Focarino
*Commissioner for Patents of the United States Patent and Trademark Office*